United States Patent [19]

Hergeth

[11] Patent Number: 4,854,171
[45] Date of Patent: Aug. 8, 1989

[54] APPARATUS FOR DETECTING EXTRANEOUS COMPONENTS IN A TEXTILE FIBER PREPARATION INSTALLATION

[76] Inventor: Hubert Hergeth, Kockerellstrasse 3, 5100 Aachen, Fed. Rep. of Germany

[21] Appl. No.: 164,105

[22] Filed: Mar. 4, 1988

[30] Foreign Application Priority Data

Mar. 13, 1987 [DE] Fed. Rep. of Germany ....... 3708188

[51] Int. Cl.$^4$ ............................................. G01N 29/04
[52] U.S. Cl. ........................................ 73/572; 73/570
[58] Field of Search .................... 73/572, 579, 570; 340/683, 674

[56] References Cited

U.S. PATENT DOCUMENTS 3,798,626 3/1974 Weichbrodt et al. .............. 340/683
4,231,258 11/1980 Menju et al. ........................... 73/572
4,392,214 7/1983 Marini et al. ............................ 73/572

FOREIGN PATENT DOCUMENTS 5226245 2/1977 Japan ..................................... 73/572

Primary Examiner—Stewart J. Levy
Assistant Examiner—Louis M. Arana
Attorney, Agent, or Firm—Herbert Dubno

[57] ABSTRACT

The presence of extraneous materials such as polypropylene strings or strands in textile fiber material is detected at the bale shaver or plucker in which tufts of the textile fiber are removed from the bale by a rotary plucker head. The plucker head is received in a suction removal hood so that a strand which tends to be wound on the head will impact upon the hood and the frequency of such impact is automatically detected and, if found to be related to the frequency of rotation of the head, automatically causes shut down of the machine to enable clearing of the extraneous fiber or string from the head.

4 Claims, 3 Drawing Sheets

APPARATUS FOR DETECTING EXTRANEOUS COMPONENTS IN A TEXTILE FIBER PREPARATION INSTALLATION

FIELD OF THE INVENTION

My present invention relates to an apparatus for detecting extraneous fibrous material in the preparation of textile fibers for further processing and, more particularly, in conjunction with bale shaving or plucking.

BACKGROUND OF THE INVENTION

In a textile fiber preparation installation, textile fibers which are pressed into bales and delivered in this form are opened up into small tufts, mixed and, if required, cleaned.

Metal parts, e.g. of harvesting and processing machines, are occasionally encountered in the textile bales. These metal parts can cause mechanical damage or fires in the preparation installation. In the textile industry, these metal parts have for about the last twenty years been detected and removed by means of induction coils. It has hitherto not been possible to detect non-ferrous extraneous components such as stones, aluminum, plastics and glass.

So-called extraneous fiber represent a further major problem for spinning works. These include pieces of fabric or tapes of other fiber in the bale. Pieces of jute or polypropylene sack wrapping are, for example, found in the bales. Other items include headscarves in cotton bales or cotton strings in cotton bales. Cotton strings or jute fiber in cotton fiber give rise to numerous thread breaks on the processing machines or may even damage the latter.

It is possible for a piece of polypropylene wrapping material in a cotton mixture to proceed unnoticed through the further processing stages. Only when the finished article of clothing is being dyed or pressed does the polypropylene fibre melt, ruining the articles of clothing. This occurence can lead to a high level of complaints.

The problems associated with extraneous fibers have risen steeply with the increase in automatic bale preparation since the beginning of the Sixties. To date, there is not a single device capable of removing such extraneous fibers on the market.

OBJECT OF THE INVENTION

It is the object of the invention to detect non-ferrous components and extraneous fibers in a textile fiber preparation installation in a simple manner.

SUMMARY OF THE INVENTION

According to the invention this is achieved by detecting and evaluating shock waves inside a processing installation. According to the invention, the shock waves caused by non-fibrous components or textile formations are detected and evaluated. The shock waves arise when textile fibers and extraneous components or extraneous textile formations are moved at high speed. The speed is more than 3 m per second. The mode of operation may be explained with reference to two typical applications:

The first application serves to detect extraneous components such as metals, stones plastics. Here, a detector is attached to a fiber transport pipe of a type commonly found in fiber preparation installations. The pipes, which generally have a diameter of 300 mm, frequently have a span of several meters between the bearing points. Fibers are transported through the pipes with the aid of an air stream. The velocity of the air stream is generally between 8 and 16 m per second. Components carried along with the fibers are transported in "jumps" in the pipeline and generate audible bangs on the pipeline. The bangs are detected by means of a detection device attached to the pipeline. The bangs are also particularly clear at pipe bends, at which the extraneous components bang against the outer pipe bend. The shock can also be detected here by a detection device.

A second typical application for the invention is in the case of so-called bale shavers. These machines are used to remove fibers in the form of tufts from bales arranged in rows. The removal of the tufts is performed by means of at least one shaving roller, from which the material is continuously sucked by a suction-removal hood: if the ble contains strings or pieces of wrapping such as, for example, parts of a polypropylene sack wrapping, these are taken up by the shaving roller. Since the textile formations taken up have a greater length than the fiber tufts, these formations wrap around the roller and are not flung off directly into the suction-removal hood. The loose ends of the formation is flung round with the beater roller in a wider beating circle than the bearer roller. During this movement the loose end bangs against the suction-removal hood. If the suction-removal hood is constructed as a resonant body, a clear banging is audible. The resonant body is constructed by using largearea, thin (0.5-4 mm) metal sheets. The frequency of the bangs corresponds to the speed of the roller or a multiple thereof. The bang (shock wave) is preferably detected at the suction-removal hood. If an extraneous fiber formation is detected and evaluated, the machine is automatically switched off immediately. An operator must remove the extraneous fiber formation. If the extraneous fiber formation were not detected and removed, it would be disintegrated into fibers by the constant banging and the extraneous fibers would get into the mixture.

A bang is detected by the shock on the pipe wall or the suction-removal hood. This can be done directly by attaching a vibration measuring device (e.g. a vibrometer) or a microdisplacement-measuring device, e.g. a device operating by the inductive or eddy current method. The measurement may also be carried out indirectly by measuring the noise of impact (sound waves) by means of a microphone. The microphone does not necessarily have to be directly attached to the conveying pipe or the suction-removal hood. The measurement may be carried out at a certain distance. To detect a foreign body or extraneous formation, the shock waves measured must be evaluated.

The shocks measured can be evaluated by their intensity, their frequency and the combination thereof. In the case of evaluation in pipes and pipe bends, evaluation by measuring the intensity is preferred. When a particular deflection of the vibrometer, microsensor or microphone is reached, the evaluation unit switches. The installation is stopped automatically or the flow of material diverted via a pipe path switcher. In the evaluation of windings on the shaving roller a combination of intensity, frequency and also multiple measurements will be advantageous. The evaluation switches when shock waves greater than a predetermined intensity and having a frequency greater than the speed of the rollers, e.g. 10 times in succession, are measured. The shaving machine is then switched off automatically.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
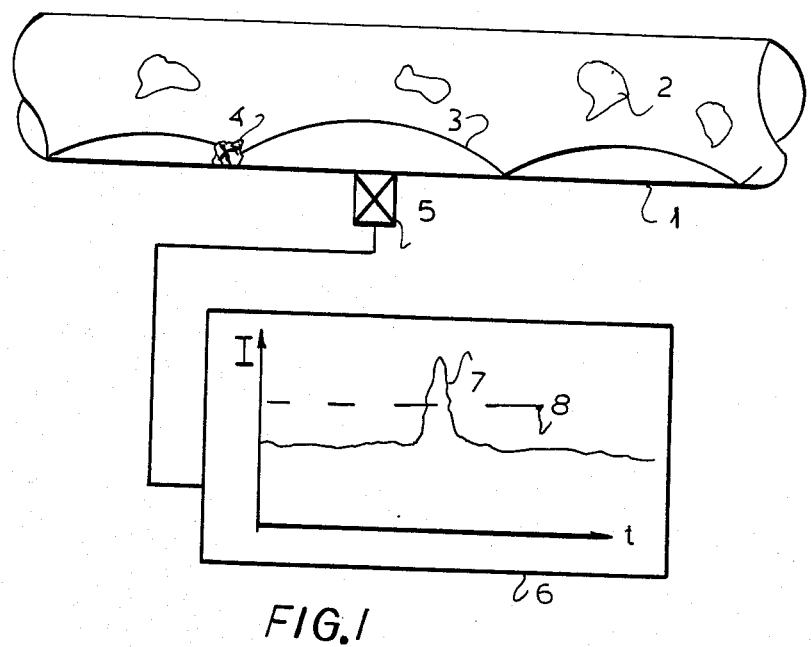
FIG. 1 is a diagram illustrating application of the principles of the invention to a pipeline in which the impact of extraneous fibers against a pipeline wall is measured according to the invention.

FIG. 1 shows a pipeline 1 in diagrammatic form through which fiber tufts 2 are transported. However, extraneous particles 4 are also carried along in the pipeline and their trajectory is indicated by lines 3. The shocks of the pipe wall are detected by a sensor 5. The diagram 6 is a graph of the intensity I measured by the sensor against time t. The impact of the extraneous particle causes a peak 7, which lies above a predetermined nominal level 8. The exceeding of the level triggers an alarm or a switch.

Figure 2:
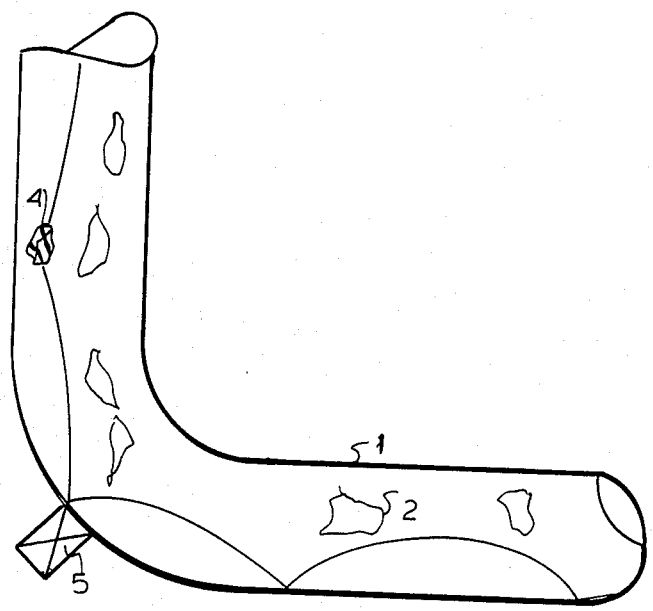
FIG. 2 is a view similar to FIG. 1 showing the invention applied to a pipe bend.

FIG. 2 shows the arrangement of the sensor 5 in a pipe bend and the trajectory 3 of the extraneous particle 4.

Figure 3:
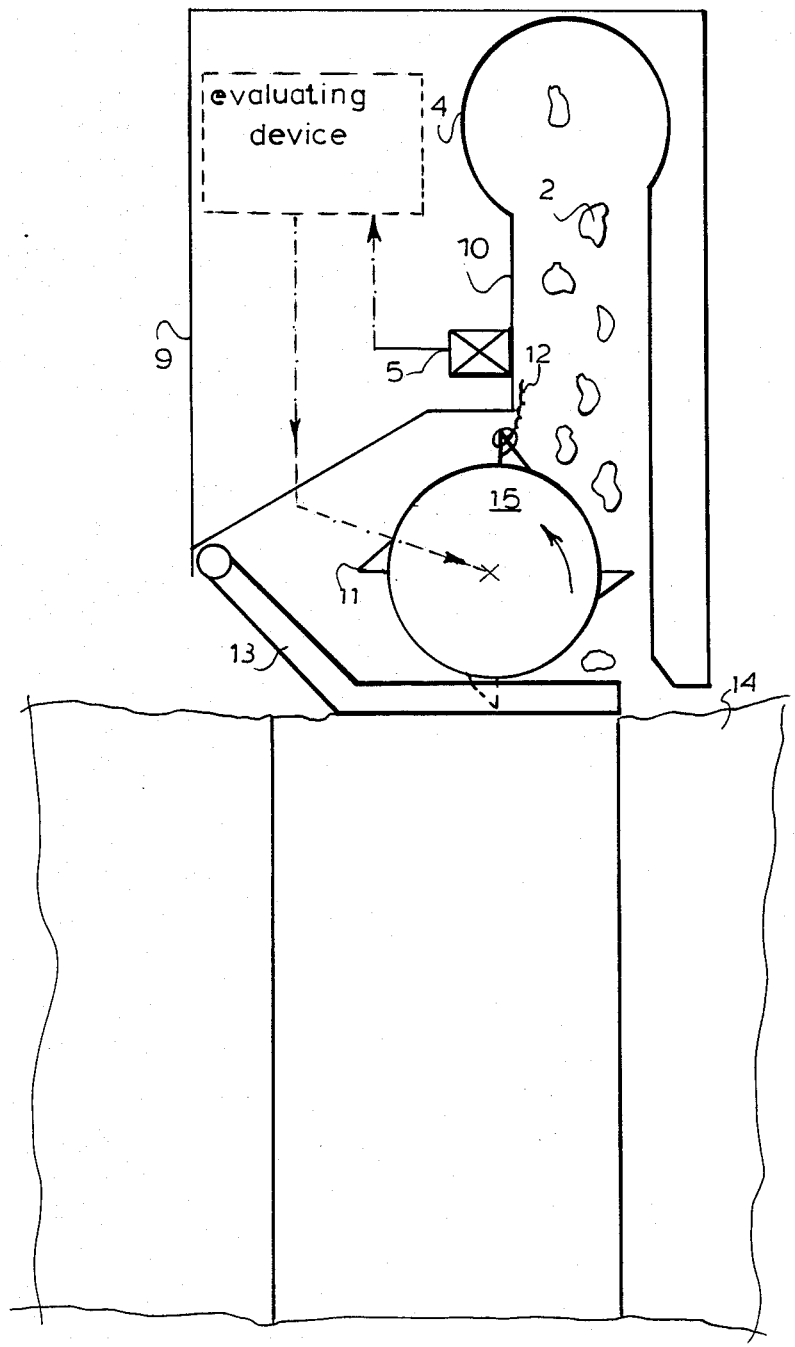
FIG. 3 is a highly diagrammatic view representing a cross section through a bale shaver or plucker adapted to form tufts of fiber from a bale, also utilizing the principles of the invention.

FIG. 3 diagrammatically represents a cross-section of the shaving head 9 of a bale shaver. Tufts 2 are flung out of bales 14 by means of shaving blades 11 on a rotary plucker head or shaving roller 15. The tufts are directed into a pipeline 4 by means of a suction-removal hood 10. 13 indicates a grid for retaining the bales. In FIG. 3 a piece of string 12 which has wound itself round a shaving blade 11 on the roller can be seen. On rotation of the cutting roller, the loose end of the string bangs against the suction-removal hood 10 and generates shocks, which are deteced by a sensor 5.

Figure 4:
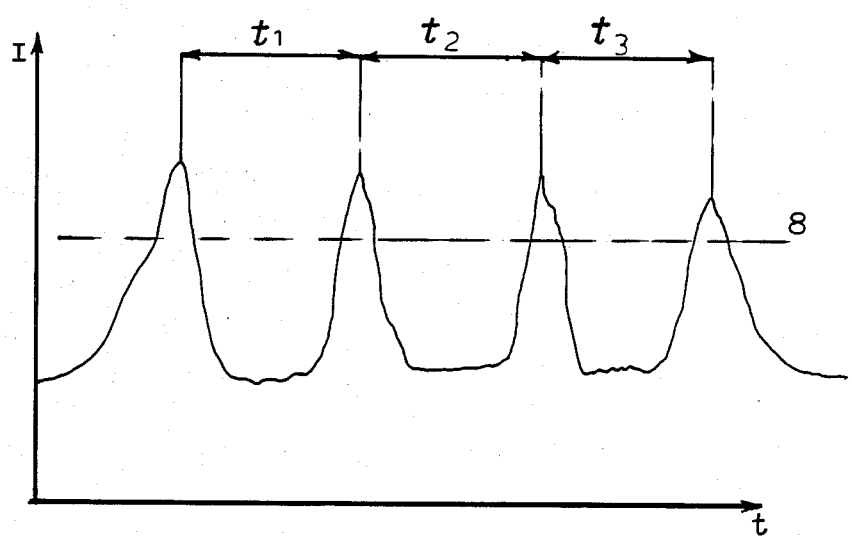
FIG. 4 is a graph diagrammatically illustrating the phenomenon detected with the apparatus of FIG. 3.

FIG. 4 is a graph of the bump measurement intensity diagrammatically according to time t. The peaks and intensity. 7 represent the individual shocks by the string on the suction-removal hood. The times t1, t2, t3 correspond approximately to the time required for one revolution of the shaving roller. The frequency is measured when the intensity has exceeded a set level 8. The times between the individual peaks t1, t2, t3 correspond approximately to the time required for one revolution of the roller.

I claim:

1. An apparatus for detecting the presence of extraneous components in textile fiber which comprises in combination:

a bale plucker having a plucker roller adapted to contact a bale of said textile fiber for removing tufts of the textile fiber from said bale and means for entraining the removed tufts away from said bale, strands of extraneous components attaching to said roller and generating impacts upon rotation thereof, said means for entraining including a duct having a wall impacted by said strands attaching to said roller;

sensing means selected from a vibration sensor and a displacement sensor on a wall of said duct for automatically detecting impacts generated by strands attached to said roller; and means connected to said sensing means for stopping said plucker upon detection of a frequency of impacts greater than a predetermined intensity which exceeds the speed of the roller.

2. The apparatus defined in claim 1 wherein said plucker includes a suction hood enclosing said roller and forming said duct, whereby said strands impact upon said hood on rotation of said roller.

3. The apparatus defined in claim 2 wherein said sensing means is a vibration measuring device on said hood.

4. The apparatus defined in claim 2 wherein said sensing means is a displacement measuring device on said hood.

* * * * *